United States Patent
Maehana (10) Patent No.: US 12,066,438 B2
(45) Date of Patent: Aug. 20, 2024

(54) METHOD FOR DETECTING CAUSATIVE BACTERIUM OF MASTITIS

(71) Applicant: ASAHI KASEI KABUSHIKI KAISHA, Tokyo (JP)

(72) Inventor: Koji Maehana, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 421 days.

(21) Appl. No.: 17/298,327

(22) PCT Filed: Nov. 29, 2019

(86) PCT No.: PCT/JP2019/046747
§ 371 (c)(1),
(2) Date: May 28, 2021

(87) PCT Pub. No.: WO2020/111223
PCT Pub. Date: Jun. 4, 2020

(65) Prior Publication Data
US 2022/0042990 A1    Feb. 10, 2022

(30) Foreign Application Priority Data

Nov. 30, 2018    (JP) .................................. 2018-225147

(51) Int. Cl.
*G01N 33/569* (2006.01)
*G01N 33/543* (2006.01)

(52) U.S. Cl.
CPC . *G01N 33/56938* (2013.01); *G01N 33/54388* (2021.08); *G01N 33/56916* (2013.01); *G01N 33/56944* (2013.01)

(58) Field of Classification Search
CPC ....... G01N 33/56938; G01N 33/54388; G01N 33/56916; G01N 33/56944; G01N 33/585; Y02A 40/70
See application file for complete search history.

(56) References Cited

U.S. PATENT DOCUMENTS

| 10,151,751 | B2 | 12/2018 | Maehana et al. |
| 10,527,616 | B2 | 1/2020 | Maehana et al. |
| 10,732,179 | B2 | 8/2020 | Maehana et al. |
| 2012/0058465 | A1 | 3/2012 | Mori et al. |
| 2015/0160212 | A1 | 6/2015 | Maehana et al. |
| 2016/0313327 | A1 | 10/2016 | Maehana et al. |
| 2016/0313328 | A1 | 10/2016 | Utsumi et al. |
| 2016/0320387 | A1 | 11/2016 | Maehana et al. |
| 2017/0242007 | A1 | 8/2017 | Tomiyama et al. |
| 2017/0336398 | A1 | 11/2017 | Lin et al. |
| 2018/0172679 | A1 | 6/2018 | Kobayashi et al. |
| 2018/0321239 | A1 | 11/2018 | Maehana et al. |
| 2019/0049446 | A1 | 2/2019 | Maehana et al. |
| 2019/0064163 | A1 | 2/2019 | Utsumi et al. |
| 2019/0079089 | A1 | 3/2019 | Maehana et al. |
| 2019/0317093 | A1 | 10/2019 | Maehana et al. |
| 2020/0103405 | A1 | 4/2020 | Utsumi et al. |

FOREIGN PATENT DOCUMENTS

| EP | 2 863 223 A1 | 4/2015 |
| EP | 3 085 769 A1 | 10/2016 |
| EP | 3 085 770 A1 | 10/2016 |
| EP | 3 085 771 A1 | 10/2016 |
| JP | 2000-266752 A | 9/2000 |
| JP | 2007-33378 A | 2/2007 |
| JP | 2012-122921 A | 6/2012 |
| JP | 2015-1398 A | 1/2015 |
| JP | 2016-31353 A | 3/2016 |

(Continued)

OTHER PUBLICATIONS

Haas et al., Associations Between Pathogen-Specific Cases of Clinical Mastitis and Somatic Cell Count Patterns, Journal of Dairy Science, vol. 87, Issue 1, pp. 95-105, Jan. 2004. (Year: 2004).*
Yu et. al., CdTe/CdS quantum dot-labeled fluorescent immunochromatography test strips for rapid detection of *Escherichia coli* O157:H7. RSC Adv., 7, 17819, Mar. 10, 2017. (Year: 2017).*
Reksen et. al., Relationships Between Milk Culture Results and Treatment for Clinical Mastitis or Culling in Norwegian Dairy Cattle. J. Dairy Sci. Vol. 89, pp. 2928-2937. 2006 (Year: 2006).*
Japanese Office Action for corresponding Japanese Application No. 2020-557851, issued May 10, 2022, including an English translation.
Extended European Search Report for corresponding European Application No. 19888823.2, dated Jul. 25, 2022.

(Continued)

*Primary Examiner* — Changhwa J Cheu (74) *Attorney, Agent, or Firm* — Birch, Stewart, Kolasch & Birch, LLP (57) ABSTRACT

An object of the present invention is to elucidate the cause of degradation of the reliability of detecting causative bacteria of environmental mastitis such as *Escherichia coli*, *Klebsiella* bacteria, *Streptococcus* bacteria, and CNS, and to provide a highly reliable detection means. Another object of the present invention is to provide a highly reliable detection means based on the immunochromatographic method, which enables quicker determination compared with the cultivation-based method, and a diagnosis kit using it. The present invention provides a method for detecting a causative bacterium of environmental mastitis of a livestock animal, which comprises: the step of determining whether number of the causative bacterium in a milk of a subject livestock animal is not smaller than a determination value defined beforehand on the basis of distribution of amounts of the causative bacterium in milks derived from a non-disease group and distribution of the amounts of causative bacterium in milks derived from a disease group by an immunological test method, and wherein the immunological test method is an immunochromatographic method using an antibody labeled with not less than $0.6/cm^2$ and not more than $3.5/cm^2$ of gold colloid particles (particle-labeled antibody).

13 Claims, 5 Drawing Sheets

(56) References Cited

FOREIGN PATENT DOCUMENTS

| | | |
|---|---|---|
| JP | 2017-032579 A | 2/2017 |
| JP | 2017-133951 A | 8/2017 |
| JP | 2018-100889 A | 6/2018 |
| WO | WO 2013/186885 A1 | 12/2013 |
| WO | WO 2015-093544 A1 | 6/2015 |
| WO | WO 2015/093545 A1 | 6/2015 |
| WO | WO 2015/093546 A1 | 6/2015 |

OTHER PUBLICATIONS

Kiku et al., "Evaluation of a rapid coliform detection kit from clinical mastitis milk using colloidal gold nanoparticle-based immunochromatographic strips," The Journal of Veterinary Medical Science, vol. 83, No. 11, 2021, pp. 1628-1633.

Nagasawa et al., "Rapid *Staphylococcus aureus* Detection From Clinical Mastitis Milk by Colloidal Gold Nanoparticle-Based Immunochromatographic Strips," Frontiers in Veterinary Science, vol. 6, Article 504, Jan. 22, 2020, pp. 1-12.

International Preliminary Report on Patentability and Written Opinion of the International Searching Authority (Forms PCT/IB/373 and PCT/ISA/237) for Application No. PCT/JP2019/046747, dated May 25, 2021, with an English translation of the Written Opinion.

Keisuke Sato et al., "Examples of Profit Improvement by Controlling Mastitis of Dairy Successors," Chuetsu Livestock Hygiene Service Center, Mar. 13, 2018, with partial English translation.

\* cited by examiner

METHOD FOR DETECTING CAUSATIVE BACTERIUM OF MASTITIS

TECHNICAL FIELD

The present invention relates to a method for detecting a bacterium that causes mastitis in milk.

BACKGROUND ART

Milk of livestock animals, of which typical examples are cow, sheep, and goat, may not be sterile, and may be contaminated with certain microorganisms due to diseases or environment. In particular, it is known that animals with a disease caused by infection of a microorganism in the udder often discharge a lot of microorganisms into milk. Typical diseases of livestock animals by infection of a microorganism include mastitis.

Mastitis is inflammation of the laticifer system or milk gland tissue, and it is caused largely by invasion, colonization, and proliferation of a microorganism in the udder. Although many kinds of animals contract mastitis, it is said that, especially concerning cow's mastitis in dairy cows, 15 to 40% of the whole dairy cows contract mastitis, and thus it is one of the extremely important diseases for dairy farmers. If a dairy cow contracts mastitis, not only the milk synthesis function is inhibited to result in reduction of lactation amount, or even stop of lactation as the case may be, but also enormous economical losses are imposed on dairy farmers, such as cost of medical treatment and penalty concerning milk price due to degradation of milk quality. Furthermore, it also increases the labor of dairy farmers, since, for example, milking of teats suffering from mastitis must be separately performed for preventing transmission.

Mastitis is caused by infection of various microorganisms. As the method for detecting such causative bacteria in milk, cultivation-based methods are widely used. However, since the cultivation-based methods require several days for obtaining a result, they are not suitable for quick identification of causative bacteria of mastitis, and therefore a technique enabling quick identification of causative bacteria of mastitis on actual dairy sites is strongly desired.

In contrast, identification methods based on an antigen-antibody reaction using an antibody directed to an ingredient specific to a causative bacterium, especially the immunochromatographic method, can provide the result in several tens of minutes, and therefore they are widely used in homes, consultation rooms, etc. as quick and convenient inspection methods (for example, Patent document 1). The immunochromatographic methods have come to be known also as methods for detecting substances contained in milk of livestock animals through the investigations of the inventors of the present invention (Patent documents 2 and 3). However, it is still common that the final judgment of diagnosis of infectious disease is done by the aforementioned cultivation-based method in this field.

PRIOR ART REFERENCES

Patent Documents

Patent document 1: Japanese Patent Unexamined Publication (KOKAI) No. 2016-31353
Patent document 2: International Patent Publication WO2013/186885
Patent document 3: Japanese Patent Unexamined Publication (KOKAI) No. 2012-122921

SUMMARY OF THE INVENTION

Object to be Achieved by the Invention

When bacteria existing in milk, especially causative bacteria of environmental mastitis such as *Escherichia coli*, *Klebsiella* bacteria, *Streptococcus* bacteria, and CNS, are detected for diagnosis and treatment of mastitis, there are sometimes samples that give positive results in diagnosis of infectious diseases performed by the cultivation-based method, but are actually negative, and thus there arises a problem that the reliability of the determination result is not necessarily high. It is thought that such a problem may also arise in the case of using the immunochromatographic method.

An object of the present invention is to elucidate the cause of degradation of the reliability of detecting causative bacteria of environmental mastitis such as *Escherichia coli*, *Klebsiella* bacteria, *Streptococcus* bacteria, and CNS, and to provide a highly reliable detection means.

Another object of the present invention is to provide a highly reliable detection means based on the immunochromatographic method, which enables quicker determination compared with the cultivation-based method, and a diagnosis kit using it.

Means for Achieving the Object

When the inventors of the present invention conducted various researches about the factors of the problem of the low reliability of the cultivation-based method mentioned above, they focused on the fact that the tendency of decrease in the reliability is more strongly observed with lower concentrations of the causative bacteria. Therefore, they presumed that the decrease of the reliability is due to the presence of the causative bacteria and bacteria contaminated from the environment in collected samples. That is, they presumed that detection of bacteria contaminated into the udder from the environment including feces and litter in addition to the causative bacteria of mastitis discharged from the mammary gland tissues might constitute the factors of the decrease in the reliability. However, it had not been confirmed whether any boundary for distinguishing normal animals and disease animals exists for amount of bacteria including causative bacteria and contaminated bacteria, and in order to conduct examinations on the assumption of presence of such a boundary, it was necessary to prepare diagnosis kits of various detection limits.

Then, the inventors of the present invention conducted various researches. During the researches, they collected milks of mastitis cows and milks of normal cows, quantitatively analyzed amounts of bacteria existing in the milks, thereby determined bacterial amount of contaminating bacteria and causative bacteria of mastitis—serving as a border that secures the reliability, and set it as a cutoff value. Further, in the detection of causative bacteria by the immunochromatographic method for diagnosing mastitis, they controlled causative bacteria detection ability by limiting amount of retained gold colloid as a constituent of the immunochromatographic device so that the detection limit corresponds to the bacterial amount as the border and thus corresponds to the aforementioned cutoff value. As a result, they developed an immunochromatographic method for detecting only the causative bacteria of mastitis without detecting bacteria contaminated from the environment, and accomplished the present invention. Thus, the present invention provides the followings.

[1] A method for detecting a causative bacterium of environmental mastitis of a livestock animal, which causative bacterium is any one selected from the group consisting of a coliform bacterium, a *Streptococcus* bacterium, and a coagulase-negative *Staphylococcus* bacterium, the method comprising:
  determining whether number of the causative bacterium in a milk of a subject livestock animal is not smaller than a determination value defined beforehand on the basis of distribution of amounts of the causative bacterium in milks derived from a non-disease group and distribution of amounts of the causative bacterium in milks derived from a disease group by an immunological test method, and
  which immunological test method is an immunochromatographic method using an antibody labeled with not less than 0.6/cm$^2$ and not more than 3.5/cm$^2$ of gold colloid particles (particle-labeled antibody).

[2] The method according to 1, wherein the determination value is not smaller than 370 cfu/ml and not larger than 1600 cfu/ml.

[3] The method according to 1 or 2, wherein the causative bacterium is any one selected from the group consisting of a coliform bacterium, a *Staphylococcus* bacterium, and a *Klebsiella* bacterium.

[4] The method according to any one of 1 to 3, wherein the subject livestock animal is a livestock animal suffering from clinical type mastitis.

[5] An immunochromatographic device comprising:
  a first part retaining a first antibody that is directed to a specific substance derived from an environmental causative bacterium of mastitis of a livestock animal, which causative bacterium is selected from the group consisting of a coliform bacterium, a *Streptococcus* bacterium, and a coagulase-negative *Staphylococcus* bacterium, and is labeled with gold colloid particles in a retention amount not less than 0.6/cm$^2$ and not more than 3.5/cm$^2$ (particle-labeled antibody), and
  a second part connected downstream from the first part, on which a second antibody directed to the specific substance is immobilized.

[6] The immunochromatographic device according to 5, wherein the determination value of the causative bacterium is not smaller than 370 cfu/ml and not larger than 1600 cfu/ml.

[7] The immunochromatographic device according to 5, wherein lower limit of the retention amount of the gold colloid particles corresponds to a determination value not smaller than 370 cfu/ml and not larger than 1600 cfu/ml defined beforehand on the basis of distribution of numbers of the causative bacterium in milks derived from a non-disease group and distribution of numbers of the causative bacterium in milks derived from a disease group.

[8] A kit for diagnosing mastitis of a livestock animal caused by an environmental causative bacterium, the kit comprising the immunochromatographic device according to any one of 5 to 7.

The present invention also provides the followings.

[1] A method for detecting a causative bacterium of environmental mastitis of a livestock animal, which comprises:
  the step of determining whether number of the causative bacterium in milk of a subject livestock animal is not smaller than a determination value defined beforehand on the basis of distribution of amounts of the causative bacterium in milks derived from a non-disease group and distribution of amounts of the causative bacterium in milks derived from a disease group.

[2] The method according to 1, wherein the causative bacterium is any one selected from the group consisting of a coliform bacterium, a *Streptococcus* bacterium, and a coagulase-negative *Staphylococcus* bacterium.

[3] The method according to 1 or 2, wherein the causative bacterium is any one selected from the group consisting of *Escherichia coli*, and a *Klebsiella* bacterium.

[4] The method according to any one of 1 to 3, wherein the determination value is not smaller than 370 cfu/ml and not larger than 1600 cfu/ml.

[5] The method according to any one of 1 to 4, wherein the determination is performed by an immunological test method using an antibody of which an antigen is a specific substance derived from the causative bacterium.

[6] The method according to 5, wherein the immunological test method is an immunochromatographic method using an antibody labeled with particles (particle-labeled antibody).

[7] The method according to 6, which uses the particle-labeled antibody in such an amount that detection lower limit corresponds to the determination value.

[8] The method according to 6 or 7, wherein the particle-labeled antibody is a gold colloid particle-labeled antibody.

[9] The method according to 8, wherein the gold colloid particle-labeled antibody is used in an amount not less than 0.6/cm$^2$ and not more than 3.5/cm$^2$ in an device for conducting an immunochromatographic method.

[10] The method according to any one of 1 to 9, wherein the subject livestock animal is a livestock animal suffering from clinical type mastitis.

[11] An immunochromatographic device comprising:
  a first part retaining a first antibody that is directed to a specific substance derived from an environmental causative bacterium of mastitis of a livestock animal and labeled with particles (particle-labeled antibody) in an amount of which lower limit is a determination value defined beforehand on the basis of distribution of numbers of the causative bacterium in milks derived from a non-disease group and distribution of numbers of the causative bacterium in milks derived from a disease group, and
  a second part connected downstream from the first part, on which a second antibody directed to the specific substance is immobilized.

[12] The immunochromatographic device according to 11, wherein the causative bacterium is any one selected from the group consisting of a coliform bacterium, a *Streptococcus* bacterium, and a coagulase-negative *Staphylococcus* bacterium, and the particle-labeled antibody is a gold colloid particle-labeled antibody, and retained in the device for conducting an immunochromatographic method in an amount not less than 0.6/cm$^2$ and not more than 3.5/cm$^2$.

[13] A kit for diagnosing mastitis of a livestock animal caused by an environmental causative bacterium, which contains the immunochromatographic device according to 10 or 11.

Effect of the Invention

According to the present invention, by using a method that can suppress influences of contaminating bacteria, or a device for the method (for example, immunochromatographic device), causative bacteria of mastitis can be quickly and conveniently detected on site with suppressing influences of contaminating bacteria from environment. The present invention enables quick identification of causative bacteria before further aggravation of pathological conditions, and thus enables decision on appropriate treatment policies such as selection of adequate antibiotics and means for prevention of infection expansion at an early stage.

MODES FOR CARRYING OUT THE INVENTION

The present invention relates to a method for diagnosing mastitis of a livestock animal caused by an environmental causative bacterium. The method of the present invention comprises the step of determining whether number of the causative bacterium in milk of a subject livestock animal is not smaller than a determination value defined beforehand on the basis of distribution of amounts of the causative bacterium in milks derived from a non-disease group and distribution of amounts of the causative bacterium in milks derived from a disease group.

[Object of Detection]

The present invention is for detecting a causative bacterium of environmental mastitis. The causative bacteria of mastitis can be roughly divided into infectious bacteria and environmental bacteria. The environmental (mastitis) causative bacteria include coliform bacteria, environmental *Staphylococcus* bacteria (*Staphylococcus* bacteria other than *Staphylococcus aureus*), and environmental *Streptococcus* bacteria (*Streptococcus* bacteria other than *Streptococcus agalactiae*). The coliform bacteria include *Escherichia coli*, *Klebsiella* bacteria, *Citrobacter* bacteria, *Enterobacter* bacteria, and *Proteus* bacteria. The *Klebsiella* bacteria include *Klebsiella pneumoniae* and *Klebsiella oxytoca*. The environmental *Staphylococcus* bacteria include CNS (Coagulase-Negative Staphylococci). CNS include *Staphylococcus intermedius*, *Staphylococcus hyicus*, *Staphylococcus xylosus*, *Staphylococcus epidermidis*, and so forth. The term "*Staphylococcus* bacterium" simply used in this specification is used to mean any one of the environmental *Staphylococcus* bacteria. The environmental *Streptococcus* bacteria include *Streptococcus uberis*, *Streptococcus agalactiae*, *Streptococcus dysgalactiae*, *Streptococcus equinus*, *Streptococcus canis*, *Streptococcus bovis*, *Streptococcus porcinus*, *Streptococcus pluranimalium*, *Streptococcus parauberis*, *Streptococcus nutans*, and *Streptococcus acidominimus*. The present invention is especially suitable for *Escherichia coli* or *Staphylococcus* bacteria.

[Determination Value]

In the present invention, a determination value defined beforehand is used for detecting a causative bacterium of mastitis. The determination value is a value for distinguishing a group of animals suffering from mastitis (disease group) and a group of animals not suffering from mastitis (non-disease group). A value used in a quantitative test for distinguishing positive and negative is generally called cutoff value, and a cutoff value is determined on the basis of test value distribution in a group of patients suffering from a specific disease and test value distribution in a group of non-patients. The determination value used for the present invention may be called cutoff value.

The determination value of the present invention is calculated on the basis of distribution of amounts of a causative bacterium in milks derived from a non-disease group and distribution of amounts of the causative bacterium in milks derived from a disease group. The determination value can specifically be obtained as explained below for cows with mastitis caused by *Escherichia coli* as an example.

Amounts of the bacterium in a plurality of milk samples obtained from the group developing mastitis caused by *Escherichia coli* (mastitis group) and a plurality of milk samples obtained from the group not developing mastitis (normal group) are determined by the cultivation-based method. In this determination, since a large number of *Escherichia coli* bacteria as environmental causative bacteria originally exist in the environment including feces or litter, they easily contaminate milk from the environment during milking, and are often detected in samples. Therefore, a certain amount of the bacterium is also detected in the samples obtained from the normal group at a certain frequency. On the basis of the distributions of the amounts of the bacterium obtained for the groups, an amount of the bacterium in milk that enables distinction of the normal group and the mastitis group can be determined as the determination value. In order to determine an effective determination value, the ROC analysis can be performed.

The ROC analysis is an analysis method using an ROC curve (Receiver Operating Characteristic curve), and is generally used for searching for an appropriate cutoff value for certain test data. The details are as follows. If a cutoff value for positive and negative is changed stepwise from the minimum value to the maximum value for one screening method, the false positive rate (=1−specificity) and sensitivity also change from 0 to 1. By plotting false positive rate in abscissa versus sensitivity in ordinate, a curve corresponding to the change of the cutoff value (POC curve) can be drawn. The cutoff value corresponding to the upperleftmost point on the curve (point nearest to (0, 1) on the graph, that is, false positive rate and sensitivity are ideally 0 and 1, respectively) is judged to be most effective as the point that divides positive and negative, and thus a cutoff value appropriate for a certain kind of test values can be obtained. The sensitivity means probability of correctly judging those to be judged positive as positive, and is represented as number of true positive/total number of objects that are truly positive (namely, number of truly positive+number of false negative). The specificity means probability of correctly judging those to be judged negative as negative, and is represented as number of true negative/total number of objects that are truly negative (namely, number of truly negative+number of false positive). As the determination value used in the present invention, a value determined by such ROC analysis as mentioned above as the most effective cutoff value can be used.

According to the examinations of the inventors of the present invention, in the case of environmental mastitis, the determination value of the bacterial amount in a milk sample can be a value not smaller than 300 cfu/ml and not larger than 3000 cfu/ml, preferably not smaller than 370 cfu/ml and not larger than 1600 cfu/ml, for any type of the causative bacterium. When the causative bacterium is a coliform bacterium, for example, *Escherichia coli*, the determination value is more preferably a value not smaller than 660 cfu/ml and not larger than 1360 cfu/ml, still more preferably not smaller than 700 cfu/ml and not larger than 900 cfu/ml. When the causative bacterium is an environmental *staphylococcus*, for example, *Staphylococcus* bacterium, the determination value is more preferably a value not smaller than 375 cfu/ml and not larger than 1595 cfu/ml, still more preferably not smaller than 875 cfu/ml and not larger than 1145 cfu/ml. According to the present invention, the determination value can be defined for every bacterial species, and may be defined for every environment where samples are collected.

The determination value calculated as described above can be used as the lower detection limit (lower limit of detectable number of causative bacteria) in the case of designing a specific detection means such as the immunochromatographic device to be explained later. This is because, if such a value is employed as the detection lower limit, positive and negative determination can be conducted at once on the basis of determining whether the object bacteria are detected or not with such an device.

According to the present invention, a determination value defined on the basis of distribution of amounts of a causative bacterium detected in milks derived from a non-disease group and distribution of amounts of the causative bacterium in milks derived from a disease group is used for diagnosing environmental mastitis, and therefore influences of the bacteria contaminated from the environment can be eliminated. Any detection means optimized as described above in consideration of influences of the environment has not exist so far to date, and is proposed for the first time by the present invention.

[Immunological Method, Immunochromatographic Method, and Immunochromatographic Device]

The method using the determination value of the present invention can be performed as a method for detecting a causative bacterium of environmental mastitis of a livestock animal, and can also be performed as a method for diagnosing environmental mastitis of a livestock animal. These methods may include the step of collecting milk from a livestock animal. The method using the determination value of the present invention can also be performed with various kinds of immunological methods using an antibody of which antigen is a specific substance derived from a causative bacterium. Examples of the immunological measurement method include, for example, immunochromatographic method, agglutination reaction method, enzyme immunoassay (ELISA), radioactive immunoassay (RIA), fluoroimmunoassay (FIA), and so forth, but it is not limited to these. When an immunochromatographic method is used, the method can be typically performed as follows.

An antigen-antibody reaction can be detected by the sandwich assay using a "labeled first antibody directed to a specific substance" retained by a first part, and a "second antibody directed to the specific substance" immobilized on a second part. Alternatively, an antigen-antibody reaction may also be detected by the competitive method using a labeled specific substance retained by a first part, and an antibody directed to the specific substance immobilized on a second part. However, in the present invention, the sandwich assay method is preferred, since it shows high detection sensitivity and gives a line indicating detection of antibody when the assay result is positive.

Figure 3:
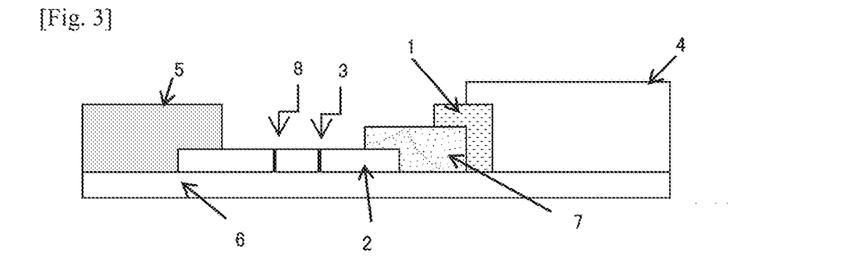
FIG. 3 A schematic sectional view of the test strip of the immunochromatographic device used in the examples is shown.

The immunochromatographic device is for detecting a specific substance in milk or for diagnosing mastitis of a livestock animal by an immunochromatographic method. Specifically, the immunochromatographic device is a device comprising a test strip having a first part retaining a labeled first antibody directed to the specific substance, or the specific substance that is labeled, a second part connected downstream from the first part, on which a second antibody directed to the specific substance is immobilized, and a third part connected upstream from the first part or the second part and having voids enabling removal of milk fat globules contained in the milk. As a specific example of the structure of the test strip, the structure of the test strip of which schematic sectional view is shown in FIG. 3 can be mentioned. In FIG. 3, a member 7 for removal of fat globules (third part) is disposed downstream from a filter member 4 for sample addition, downstream from a labeled antibody-impregnated member (first part) 1, and upstream from a membrane carrier 2 for chromatographic development (second part). In FIG. 3, the second part also has a capturing part 3 (test line) on which the second antibody directed to the specific substance is immobilized, and which captures the specific substance bound with the labeled first antibody, and a capturing part 8 (control line) that captures a substance serving as a control for confirming that the reaction has normally advanced on the device.

The immunochromatographic device can be produced in a known manner by using marketed materials.

The material used for the first part is not particularly limited, so long as a material enabling immunochromatography is chosen, but preferred examples include a fiber matrix of cellulose derivative etc., filter paper, glass fiber, cloth, cotton, and so forth.

The material used for the second part is not particularly limited, so long as a material enabling immunochromatography is chosen, but preferred examples include nitrocellulose, mixed nitrocellulose ester, polyvinylidene fluoride, nylon, and so forth.

The material used for the third part preferably has voids that enable removal of milk fat globules contained in milk and having a diameter of about 1 to ten and several micrometers. The third part must be disposed upstream from the aforementioned second part consisting of a porous membrane having a pore diameter of several tens to several hundreds nm, and is preferably disposed on the upstream side of the first part, i.e., at a position at which the sample solution can contact with and pass through the device for the first time.

The voids of the third part may have a size that enables removal of milk fat globules, and retention particle size is preferably 0.1 to 10 µM, more preferably 1 to 3.5 µm. The material thereof is not particularly limited, so long as a material having voids within the aforementioned range is chosen, but it is preferably a fiber matrix of cellulose derivative or the like, filter paper, glass fiber, cloth, cotton, or the like. The retention particle size means such a particle size of milk fat globules that milk fat globules having a particle size not smaller than the retention particle size cannot pass through the voids and retained by the third part, and substantially corresponds to average pore size of the voids of the third part, and 50% or more, preferably 60% or more, more preferably 70% or more, still more preferably 80% or more, particularly preferably 90% or more, most preferably 98% or more, of milk fat globules having a particle size not smaller than the retention particle size cannot pass through the voids and are retained by the third part. Ratio of milk fat globules to be retained can be measured by a method well known to those skilled in the art. For example, the product catalogue of GF/B provided by GE Healthcare Bioscience describes that the retention particle size (particle diameter for which retention efficiency is 98%, the term retention particle size used in this specification has this meaning, unless especially indicated) thereof is 1.0 µm, and such a particle size as mentioned above can be confirmed by a method well known to those skilled in the art.

For the aforementioned third part, only a material having a specific retention particle size may be used, or materials having specific retention particle sizes decreasing stepwise and adhered together may be used in order to enhance the separation efficiency for milk fat globules. Such a third part as mentioned above constituted by two or more kinds of members having voids that can remove milk fat globules of different particle sizes, respectively, constitutes a preferred embodiment of the present invention, and such a third part as mentioned above constituted by a first member disposed downstream and a second member disposed upstream, wherein the retention particle size of the second member is larger than the retention particle size of the first member, constitutes a more preferred embodiment of the present invention. When the third part is constituted by two kinds of members, it is preferred that the retention particle size of the first member disposed downstream is 1.0 to 2.0 µm, and the retention particle size of the second member disposed upstream is 3.0 to 3.5 µm. In order to detect a specific substance at high sensitivity from milk containing milk fat globules having a large particle size distribution at a high concentration, preferably milk not diluted after milking, it is preferred that the third part is constituted with a combination of a member having a small retention particle size and a member having a large retention particle size.

The aforementioned first part retains a labeled first antibody directed to a specific substance, or the specific substance that is labeled. If a labeled first antibody directed to a specific substance is retained on the first part, the specific substance can be detected by the sandwich assay method. If a labeled specific substance is retained on the first part, the specific substance can be detected by the competitive method. For the present invention, the sandwich assay method that provides high detection sensitivity and an antibody detection line representing positive result is preferred, and therefore it is preferred that the first part retains a labeled first antibody directed to a specific substance.

When the first part is made to retain a labeled first antibody directed to a specific substance, two kinds of antibodies, a first antibody directed to the specific substance, and a second antibody directed to the specific substance, are used. The aforementioned first antibody and second antibody are antibodies that can simultaneously bind to the specific substance so that the specific substance can be detected by the sandwich assay method, and the epitope of the specific substance to be recognized by the aforementioned first antibody is preferably different from the epitope of the specific substance to be recognized by the aforementioned second antibody.

In the present invention, in order to obtain a detectable signal, the first antibody or the specific substance retained on the first part is labeled. Examples of the label used for the present invention include a colored particle, enzyme, radioisotope, and so forth, and it is preferable to use a colored particle that can be visually detected without any special equipment. Examples of the colored particle include metal microparticles such as those of gold and platinum, nonmetallic particles, latex particles, and so forth, but are not limited to these. The colored particle may have any size so long as the colored particle has such a size that it can be transported downstream through the inside of the voids of the test strip, but it preferably has a size of 1 nm to 10 µm, more preferably 5 nm to 1 µm, still more preferably 10 to 100 nm, in diameter.

By changing concentration of the particles, the lower detection limit of the immunochromatography can be controlled. The particle concentration can be measured on the basis of the maximum absorbance at 500 to 600 nm. Then, the particles can be impregnated into a substrate and the substrate can be dried. Examples of material suitable for such a conjugate pad include paper, cellulose mixture, nitrocellulose, polyester, acrylonitrile copolymer, glass fiber, and non-woven fabric such as rayon non-woven fabric, but it is not limited to these. A pad made of glass fibers is preferably used.

The particle concentration is desirably $0.1/cm^2$ or higher, more preferably $0.3/cm^2$ or higher, still more preferably $0.6/cm^2$ or higher, in terms of value of the maximum absorbance, from the viewpoint of ability for maintaining reactivity in the sample. Further, from the viewpoint of liquid flow during the immunochromatography or visibility on nitrocellulose, it is desirably $10/cm^2$ or lower, more preferably $5/cm^2$ or lower, still more preferably $4/cm^2$ or lower.

In the present invention, the test strip mentioned above may be used as it is as the immunochromatographic device, or may be stored in a case and used as the immunochromatographic device. The device of the former case can be preferably used when milk used as a sample can be used in a large volume by directly dipping one end of the test strip into the sample contained in a container. The device of the latter case can be preferably used when the volume of milk used as a sample is small by quantifying a predetermined volume of the sample with a pipet or the like, and dropping it to the test strip. In the latter case, the shape of the case may be any shape so long as the test strip can be stored in it. The material of the case may be any kind of material, but preferred examples include polypropylene, polycarbonate, and so forth.

The immunochromatographic device of the present invention can also be provided as a kit comprising a container such as micro tube, and a solution for addition such as solution for addition containing a lytic enzyme or surfactant for lysing bacteria to elute the ribosomal protein L7/L12 into the solution in combination. The kit provided by the present invention is for detecting a specific substance in milk, or for diagnosing mastitis of a livestock animal.

[Specific Substance and Antibody for which Antigen is Specific Substance]

When the method of the present invention is performed by an immunological method using an antibody of which antigen is a specific substance derived from a causative bacterium, the specific substance may be any substance so long as it can be measured by the immunological method, but it is preferably an ingredient of a bacterium or substance secreted by a bacterium. It is more preferably the bacterial L7/L12 ribosomal protein. Since a large number of copies of the L7/L12 ribosomal protein exist in the cells, it can be detected at high detection sensitivity. By the known method described below, an antibody that can distinguish a specific bacterium that causes mastitis from other bacteria at the genus or species level can actually be obtained. The type of the bacterium is not particularly limited, and may be a gram-positive bacterium or gram-negative bacterium. Examples include, for example, gram-positive bacteria including Staphylococci (bacteria belonging to the genus *Staphylococcus*) such as *Staphylococcus aureus, Escherichia coli*, bacteria belonging to the genus *Klebsiella*, and so forth, but the bacterium is not limited to these.

The aforementioned antibody can be produced by the method described in International Patent Publication WO00/06603. When the bacterial ribosomal protein L7/L12 is used as the antigen, the antibody can be produced by using the full length protein or partial peptide of the bacterial ribosomal protein L7/L12 as an antigen, but it is preferably produced by using the full length protein as the antigen. By inoculating this partial peptide or full length protein to an animal as it is or after it is cross-licked with a carrier protein, in combination with an adjuvant as required, and collecting serum of the animal, an antiserum containing antibodies that recognize the L7/L12 ribosomal protein (polyclonal antibody) can be obtained. The antibodies can also be purified from the antiserum and used. Examples of the animal for the inoculation include sheep, horse, goat, rabbit, mouse, rat, and so forth, and sheep, rabbit, and so forth are preferred especially when polyclonal antibodies are produced. It is more preferable to use an monoclonal antibody obtained by a known method comprising producing a hybridoma cell as the antibody, and in this case, the animal is preferably mouse. By obtaining a monoclonal antibody that reacts with the ribosomal protein. L7/L12 of a specific bacterium that causes mastitis, but does not react with the ribosomal protein L7/L12 of bacteria that cause mastitis, but are other than the foregoing specific bacterium, through screening, it can be usefully utilized for diagnosis of determining whether a subject suffers from infectious diseases caused by the bacterium.

If the antibody is a monoclonal antibody that reacts with an ingredient of a specific bacterium that causes mastitis or a substance that is secreted by the bacterium, but does not react with an ingredient of another bacterium that causes mastitis, which is other than the aforementioned specific bacterium, or a substance that is secreted by this bacterium, it can be used even if it is an antibody that recognizes a substance other than the ribosomal protein L7/L12 as the antigen.

It is preferable to use a monoclonal antibody of which antigen-antibody reaction is not inhibited by any contaminants contained in milk other than the specific substance as the monoclonal antibody. For example, milk contains a large amount of proteins such as casein, and they may inhibit the reaction of the specific substance and the monoclonal antibody. When a monoclonal antibody for a specific substance is produced by a conventional method, it may be preferable to appropriately choose and use a monoclonal antibody of which antigen-antibody reaction is not inhibited by, for example, casein and so forth, or a monoclonal antibody of which antigen-antibody reaction is not significantly influenced by such substances. Such a monoclonal antibody can be easily obtained by producing a monoclonal antibody that specifically reacts with an antigen by a usual method, then examining whether the antigen-antibody reaction of the monoclonal antibody is inhibited by the presence of a contaminant such as casein, and choosing a monoclonal antibody of which reaction is not substantially inhibited.

[Label of First Antibody and Gold Colloid Particles]

In the present invention, in order to obtain a detectable signal, the first antibody or specific substance retained on the first part is labeled. Examples of the label used in the present invention include a colored particle, enzyme, radioisotope, and so forth, but it is preferable to use colored particles that can be visually detected without requiring any special equipment. Examples of such colored particles include fine particles of metal such as gold and platinum, nonmetallic particles, latex particles, and so forth, but they are not limited to these. The colored particles may have any size so long as they can be conveyed downstream through the inside of the voids of the test strip, but the diameter thereof is preferably 1 nm to 10 μm. The diameter is more preferably 5 nm to 1 μm, still more preferably 10 nm to 100 nm. Preferred examples of the colored particles include gold colloid particles.

In a preferred embodiment of the present invention, an immunochromatographic device designed so that the detection limit of the device corresponds to the determination value mentioned above, which is defined beforehand, is used. In such an embodiment, a gold colloid particle-labeled antibody is used as the labeled first antibody retained on the labeled antibody-impregnated member (first part). In this case, the detection limit can be adjusted by controlling the amount of the retained gold colloid particle-labeled antibody (it may henceforth simply referred to as "gold colloid retention amount"). By increasing the gold colloid retention amount, the detection limit can be made lower, and the detection limit can be made higher by reducing the gold colloid retention amount.

The gold colloid retention amount of the labeled antibody-impregnated member of the immunochromatographic device can be represented as Amax/cm$^2$. Specifically, by cutting out the labeled antibody-impregnated member retaining gold colloid in the device, and adding it to 0.2 ml of water or buffer contained in a tube, gold colloid is eluted. The maximum absorbance Amax of the obtained solution is measured at 500 to 600 nm, for example, 540 nm, using a cell of which optical path length is 1 cm. By dividing the obtained measured value with the area of the glass fibers used for the elution, the value of Amax/cm$^2$ is calculated.

According to the examinations of the inventors of the present invention, the retention amount of the gold colloid contained in the labeled antibody-impregnated member of the immunochromatographic device may be, in terms of the value of A540max/cm$^2$, for example, 0.3 or larger and 6.0 or smaller or 0.6 or larger and 3.8 or smaller, preferably 0.8 or larger and 3.5 or smaller, more preferably 1.0 or larger and 3.0 or smaller or 1.0 or larger and 2.0 or smaller, still more preferably 1.5 or larger and 2.5 or smaller. Such a determination value can be preferably used for the case where the causative bacterium is a coliform bacterium or *Staphylococcus* bacterium, and it can be more preferably used for the case where the causative bacterium is *Escherichia coli*.

[Lysis of Bacteria in Sample]

When an immunological method using a specific substance derived from a causative bacterium as an antigen is used for detecting the causative bacterium according to the present invention, it is necessary to highly efficiently lyse the bacterial cells to release the antigen in the cells to the outside of the cells. However, when milk is used as a sample, cell lysis is not sufficiently attained by conventional methods in many cases because of influences of proteins such as casein, milk fat globules, and so forth contained in milk in large amounts. Therefore, a lysis agent containing an enzyme and a surfactant can be used as required.

Lysis Agent

Examples of the enzyme contained in the lysis agent include lysozyme, lysostaphin, labiase, β-N-acetylglucosaminidase, and so forth. Content of the lytic enzyme contained in the lysis agent (when a plurality kinds of lytic enzymes are used, content as the total amount of the lytic enzymes) is not particularly limited, so long as lysis rate effective for the detection is secured.

As the surfactant, any of nonionic surfactant, and anionic surfactant can be used, or they can be used in combination, and cationic surfactant and ampholytic surfactant can also be used as required.

As the nonionic surfactant, any of those of ester ether type, ester type, and ether type can be preferably used. More specifically, examples include polyoxyethylene alkyl ethers, polyoxyethylene alkyl phenyl ethers, fatty acid sorbitan esters, alkyl polyglucosides, fatty acid diethanolamides, alkyl monoglyceryl ethers, polysorbates (formed by condensation of several tens of ethylene oxide molecules to a fatty acid sorbitan ester), and so forth, but it is not particularly limited. Especially preferred examples include polysorbates, more specifically, polyoxyethylene (20) sorbitan monolaurate, polyoxyethylene (60) sorbitan monostearate, polyoxyethylene (65) sorbitan tristearate, and polyoxyethylene (80) sorbitan monooleate, and so forth, as well as polyoxyethylene alkyl phenyl ethers, more specifically, polyoxyethylene (10) octyl phenyl ether, and so forth.

As the anionic surfactant, any of carboxylic acid salts, sulfonic acid salts, sulfuric acid ester salts, and others can be preferably used. More specific examples include alkyl ether carboxylates, linear alkylbenzenesulfonates (LAS), α-olefinsulfonates (AOS), dialkylsulfosuccinates, formaldehyde condensates of naphthalenesulfonate, alkylsulfuric acid ester salts (AS), polyoxyethylenealkylsulfuric acid ester salts (AES) obtained by addition of ethylene oxide to a higher alcohol and following sulfation, phosphoric acid ester salts of a higher alcohol or ethylene oxide adduct thereof, and so forth. Further specific examples include sodium alkylsulfates such as sodium dodecylsulfate and sodium myristylsulfate, sodium N-acylsarcosinates such as sodium N-lauroylsarcosinate and sodium N-myristoylsarcosinate, sodium dodecylbenzenesulfonate, hydrogenated coconut fatty acid monoglyceride monosodium sulfate, sodium laurylsulfoacetate, N-acylglutamates such as sodium N-palmitoylglutamate, N-methyl-N-acylalanine sodium, and sodium α-olefinsulfonates.

As the cationic surfactant, any of those of amine salt type and quaternary ammonium salt type can be preferably used. More specific examples include distearyldimethylammonium chloride, benzalkonium chloride, hexadecyltrimethylammonium bromide, hexadecyltrimethylammonium bromide, myristyltrimethylammonium bromide, and so forth.

Examples of the ampholytic surfactant include those of amino acid type (alkylaminofatty acid salts), betaine type (alkyl betaines), amine oxide type (alkylamine oxides), and so forth, but it is not particularly limited. More specific examples include dimethylammoniopropanesulfonates, dodecyldimethylammoniobutyrates, betaine laurate, and amidopropyl betaine. Further specific examples include n-tetradecyl-N,N-dimethyl-3-ammonio-1-propanesulfonate, n-decyl-N,N-dimethyl-3-ammonio-1-propanesulfonate, n-dodecyl-N,N-dimethyl-3-ammonio-1-propanesulfonate, n-tetradecyl-N,N-dimethyl-3-ammonio-1-propanesulfonate, n-hexadecyl-N,N-dimethyl-3-ammonio-1-propanesulfonate, and N-dodecyl-N,N-(dimethylammonio)butyrate.

The lysis agent may contain a buffering agent for, for example, improving reactivity. The buffering agent is not particularly limited, and examples include, as buffer, for example, Good buffer, Tris buffer, phosphate buffer, acetate buffer, borate buffer, and so forth. Although pH of the buffer is not particularly limited, it is, for example, in the range of pH 4 to 10, preferably pH 6 to 9.

The lysis agent may contain, besides the lytic enzyme and the surfactant, one or more kinds of other ingredients, so long as the intended effect is not markedly degraded. Preferred examples of the ingredients other than the lytic enzyme and the surfactant include a substance that has an effect of promoting the lysis, or an effect of suppressing non-specific reactions.

Examples of a substance that has an effect of promoting the lysis include glutaraldehyde, halogen compounds, chlorhexidine, alcohols (for example, methanol, ethanol, 1-propanol, 2-propanol, 1-butanol, 2-butanol, 2-methyl-1-propanol, and 2-methyl-2-propanol), phenol, hydrogen peroxide, acrinol, guanidine and salts thereof, chelating agents, organic acids (for example, decanoic acid) and salts thereof, polyhydric alcohols (for example, ethylene glycol, propylene glycol, diethylene glycol, glycerin, and mono monocaprylin), and reducing agents such as 2-mercaptoethanol, dithiothreitol, cystine, and thiophenol, but it is not limited to these.

For example, when either one of guanidine and a salt thereof (for example, guanidine thiocyanate) is used, as for the lower limit of the final concentration thereof at the time of mixing with milk, the concentration (when two or more kinds of the substances are used, it is the concentration as the total concentration of them, and this is also applied to the upper limit) can be 0.1 mM or higher, preferably 1 mM or higher, more preferably 1 mM or higher. In any case, as for the upper limit of the final concentration at the time of mixing with milk, the concentration can be 500 mM or lower, preferably 200 mM or lower, more preferably 100 mM or lower.

Examples of the chelating agent include ethylenediaminetetraacetic acid (EDTA) and a salt thereof, glycol etherdiaminetetraacetic acid (EGTA) and a salt thereof, polyphosphoric acid and a salt thereof, as well as metaphosphoric acid and a salt thereof. As for the lower limit of the final concentration thereof at the time of mixing with milk, the concentration (when two or more kinds of the chelating agents are used, it is the concentration as the total concentration of them, and this is also applied to the upper limit) can be 0.001 mM or higher, preferably 0.01 mM or higher, more preferably 0.1 mM or higher. In any case, as for the upper limit of the final concentration at the time of mixing with milk, the concentration can be 100 mM or lower, preferably 10 mM or lower, more preferably 5 mM or lower, from the viewpoint of suppressing inhibition of the antigen-antibody reaction.

As an additive, a salt, protein, polymer compound, antimicrobial agent, and so forth can also be used.

As the protein, especially in order to prevent reaction of the antibody used and protein A of *Staphylococcus aureus*, globulin that does not participate in the reaction with the antigen can be added. The globulin (γ-globulin) may be one derived from an animal species, for example, a mammal such as mouse, rabbit, cattle, pig, horse, sheep, and goat, bird such as chicken, or human, and it is not particularly limited. Although the γ-globulin concentration is not particularly limited, it may be 0.01 μg/ml or higher, preferably 0.1 μg/ml or higher, more preferably 1 μg/ml or higher, as the final concentration at the time of the reaction, from the viewpoint of suppressing false positive results. Further, in any case, from the viewpoint of not inhibiting the objective antigen-antibody reaction, it can be 10 mg/ml or lower, preferably 5 mg/ml or lower, more preferably 1 mg/ml or lower. Such conditions concerning the final concentration are especially suitable for the immunochromatographic method.

Lysis Conditions

Mixing ratio of milk and the lysis agent is not particularly limited, so long as the final concentrations of the lytic enzyme etc. are properly maintained, and sufficient lysis ratio can be secured. If the lysis agent is used in a volume relatively small with respect to milk, the milk is not diluted. Therefore, it can be expected that bacterial cells can be detected with higher sensitivity. When the lysis agent is used in a volume relatively large with respect to milk, influences of fat globules and proteins contained in milk are reduced, and therefore it can be expected that bacterial cells can be detected in a shorter time. From the viewpoint that a higher ratio of milk in the mixture of milk and the lysis agent (milk/(milk+lysis agent)×100) can provide higher detection sensitivity, the ratio can be, for example, 5% or higher, preferably 10% or higher, more preferably 20% or higher, further preferably 30% or higher, irrespective of the other conditions. As for the upper limit of the ratio, if the lysis agent solidified by drying or the like is used, the ratio of milk can be 100%, irrespective of the other conditions. The ratio of the milk can be 90% or lower, 80% or lower, 70% or lower, 60% or lower, or 50% or lower, irrespective of the other conditions. As for the upper limit, the ratio may be determined in consideration of ease of mixing, stability of the lysis agent as a solution, and so forth.

Temperature and time for the lysis treatment are not particularly limited, so long as the lytic enzyme used can exhibit the activity, and the temperature may usually be room temperature. The treatment time to be required after mixing of the lysis agent can be appropriately determined by those skilled in the art in consideration of lysis ratio.

EXAMPLES

[Consideration of Cutoff Value]

*Escherichia coli* cultivation-positive milk samples were divided into samples obtained from a group of dairy cows which developed mastitis (group of individuals for which clinical symptoms such as abnormalities in milk, abnormalities in the udder, and systemic symptoms were confirmed on veterinarians' diagnosis), and samples obtained from a normal dairy cow group which did not developed mastitis, and the bacterial amounts obtained in the cultivation were compared. The amounts of *Escherichia coli* in milks were obtained as follows. Milks were serially diluted if needed, inoculated on a blood agar medium or cultivation film in a volume of 10 μl to 1 ml, and incubated overnight at 37° C. The produced colonies were counted to calculate the amount of *Escherichia coli* in milk. The bacterial amounts in milks mentioned in the following experiments were measured by this method unless especially indicated.

Figure 1:
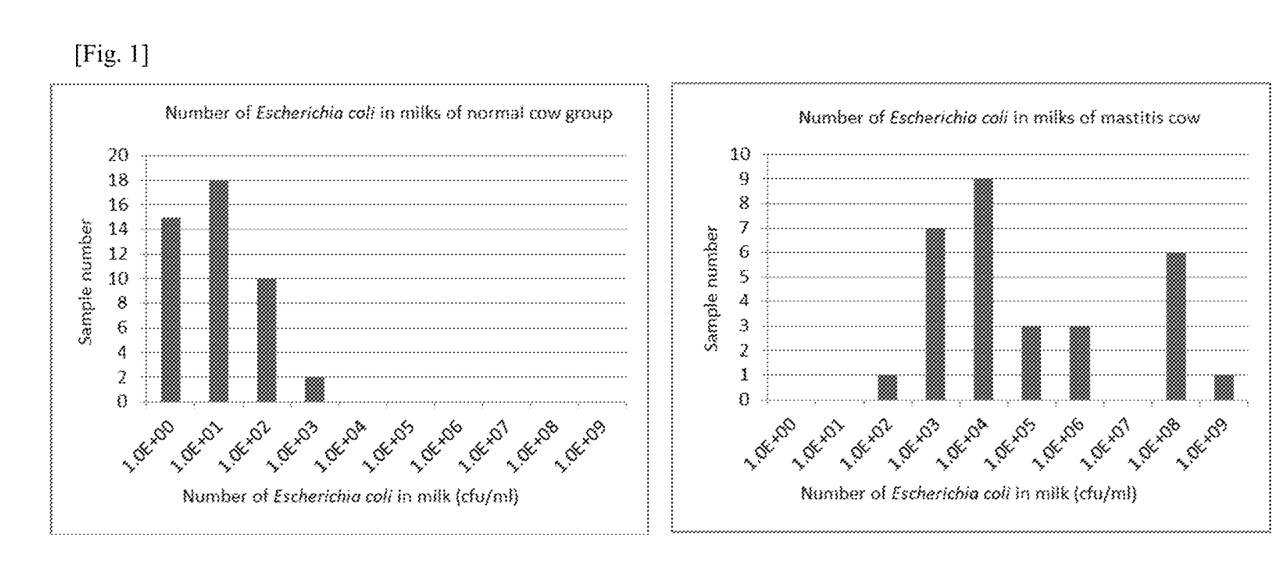
FIG. 1 Numbers of *Escherichia coli* in milks of normal cow group (left) and mastitis group (right). For example, the column of "1.0E+00" indicates the number of samples in which number of the bacterium was not smaller than $1.0 \times 10^0$ cfu/ml and lower than $1.0 \times 10^1$ cfu/ml. The same shall apply to the other columns.

Graphs showing numbers of samples for specific amounts of *Escherichia coli* for the mastitis group and normal group are shown as FIG. 1. It was found that *Escherichia coli* was also detected from the milks of the normal cows that did not suffer from mastitis in a bacterial amount of $10^0$ to $10^3$ (cfu/ml). Since a huge number of *Escherichia coli* bacteria exist in the environment including feces and litter, it easily contaminates from the environment during milking, and often detected by cultivation. On the other hand, in the milks obtained from the cows that suffered from *Escherichia coli* type mastitis, *Escherichia coli* was detected in a bacterial number of $10^3$ to $10^9$ (cfu/ml), and it was found that the distribution of bacterial numbers was greatly different from that of the bacterial numbers of the normal group.

In order to calculate the bacterial number in milk that serves as the border of the normal group and mastitis group (cutoff value), the ROC analysis was carried out for the bacterial numbers in milks of the normal group and mastitis group.

With changing the bacterial amounts in the milks of the normal group and mastitis group, sensitivity, specificity, positive predictive value, and negative predictive value were calculated by the ROC analysis.

Figure 2:
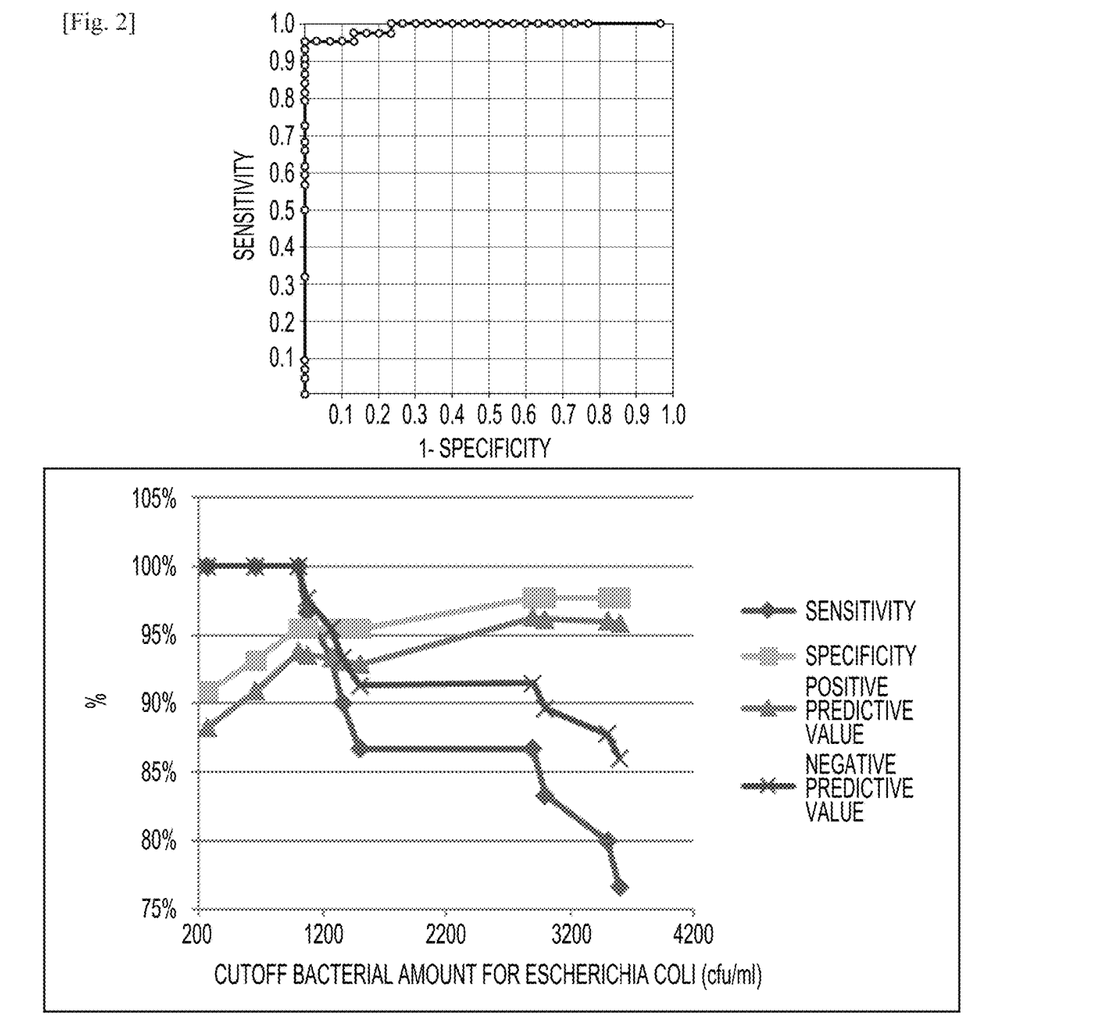
FIG. 2 A mastitis ROC curve (upper part) and a graph showing sensitivity, specificity, positive predictive value, and negative predictive value obtained for mastitis (lower part), for the case where the causative bacterium is *Escherichia coli*.

Sensitivity=Positive determined on the basis of determination value/True positive Specificity=Negative determined on the basis of determination value/True negative Positive predictive value=True positive/Positive determined on the basis of determination value Negative predictive value=True negative/Negative determined on the basis of determination value The ROC curve was shown in the upper part of FIG. 2. When bacterial amounts in milks providing a value of 90% or higher for all of sensitivity, specificity, positive predictive value, and negative predictive value were determined as the determination values for the normal group and mastitis group, the range thereof was 660 to 1360 (cfu/ml) (FIG. 2, lower part). For the calculation, statistical software StatFlex (Artec Co., Ltd.) was used.

[Preparation of Ribosomal Protein L7/L12 Antibody]

According to the method described in International Patent Publication WO00/06603, Examples, the L7/L12 ribosomal protein was obtained, and monoclonal antibodies were prepared by using this protein. As the monoclonal antibodies used for the following experiments, a combination of two kinds of monoclonal antibodies that can simultaneously bind to different sites of the L7/L12 ribosomal protein was selected.

[Preparation of Immunochromatographic Device]

An immunochromatographic device can be prepared as follows. A sectional view of the immunochromatographic device is shown in FIG. 3.

Gold Colloid Particle-Labeled Antibody-Impregnated Member

A gold colloid solution (particle size 60 nm, 9 mL, BB International) was mixed with 0.1 M potassium phosphate, pH 7.0, 1 ml of the monoclonal antibody-1 (100 μg/mL) to be labeled with gold colloid particles was added to the mixture, and the resulting mixture was left standing at room temperature for 10 minutes so that the antibody bound to the gold colloid particle surfaces. Then, a 10% aqueous solution of bovine serum albumin (BSA) was added at a final concentration of 1% in the gold colloid particle solution, so that the remaining surfaces of the gold colloid particles were blocked with BSA, to prepare a solution of the monoclonal antibody-1 labeled with gold colloid particles (henceforth referred to as "gold colloid particle-labeled antibody"). This solution was centrifuged (at 7600 rpm for 15 minutes) to precipitate the gold colloid particle-labeled antibody, and the supernatant was removed to obtain the gold colloid particle-labeled antibody. This gold colloid particle-labeled antibody was suspended in 20 mM Tris-hydrochloric acid buffer (pH 7) containing 0.25% BSA, 2.5% sucrose, and 35 mM NaCl to obtain a gold colloid-labeled antibody solution.

A glass fiber pad of a strip-like shape was impregnated with the gold colloid particle-labeled antibody solution, of which concentration was adjusted, and dried at room temperature under reduced pressure to obtain a gold colloid-labeled antibody-impregnated member 1 (first part).

Part for Capturing Complex of Antigen and Gold Colloid Particle-Labeled Antibody A nitrocellulose membrane having a width of 25 mm and a length of 300 mm was prepared as a membrane carrier 2 for chromatographic development with chromatography medium (second part). A solution containing the monoclonal antibody-2 (1.5 mg/me was applied in the shape of a line in a volume of 1 μL/cm to the membrane carrier 2 for chromatographic development at a position of 10 mm from the end on the side of the chromatographic development starting point, and dried at 50° C., and then the membrane carrier was immersed in a 0.5% sucrose solution for 30 minutes, and dried overnight at room temperature to obtain a part 3 for capturing the complex of the ribosomal protein L7/L12 antigen and the gold colloid particle-labeled antibody.

Preparation of Immunochromatographic Device

In addition to the aforementioned labeled antibody-impregnated member 1 and membrane carrier 2 for chromatographic development, 25 mm GF/DVA (filter member 4 having a thickness of 776 μm and consisting of glass fibers, retention particle size 3.5 μm, GE Healthcare Bioscience) and 20 mm GF/AVA (filter member 7 having a thickness of 299 μm and consisting of glass fibers, retention particle size 1.7 μm, GE Healthcare Bioscience) were prepared as members serving as both the member for sample addition and the member for removal of fat globules (third part), and filter paper as the member 5 for absorption was further prepared. After these members were adhered on a substrate 6 (thickness 254 μm, made of polystyrene, having adhesive for adhering the members) in the order shown in FIG. 3, they were cut in a width of 5 mm to prepare the immunochromatographic device.

[Adjustment of Detection Limit of Immunochromatography Device]

The immunochromatographic devices satisfying the conditions 1 to 5 were obtained by preparing them with changing the gold colloid retention amount.

Milks spiked with serially diluted cultured bacteria were used as samples, and detection was performed with the immunochromatographic devices satisfying the conditions 1 to 5. Specifically, 0.5 ml of a lysis treatment solution (1% (final concentration) of Triton X-100, 0.3% of sodium N-lauroylsarcosinate, 2.2 mg/ml of lysozyme, 0.1 M MOPSO, pH 7.5) and 0.3 ml of milk were put into a microtube, and left standing for 30 minutes. The immunochromatographic device was immersed into the mixed solution, chromatographic development was allowed by leaving the device standing at room temperature for 30 minutes, and then the presence or absence of capture of the complex of the ribosomal protein L7/L12 antigen and the gold colloid particle-labeled antibody by the aforementioned capturing part 3 was confirmed by visual inspection as presence or absence of a reddish purple line that became more or less conspicuous in proportion to the capture amount.

The obtained detection limits are shown in the following table. It was found that the detection limit can be adjusted by changing the retention amount of gold colloid. The retention amount of gold colloid was calculated as follows. The glass fibers as the impregnated member were cut out, added to 0.2 ml of distilled water or buffer contained in a microtube, the mixture was stirred by using a vortex mixer to elute the gold colloid, and the maximum absorbance Amax of the elution solution was measured at 540 nm. The size of the glass fibers was measured, and the value of Amax/cm$^2$ was calculated as the gold colloid retention amount.

TABLE 1

|  | Condition 1 | Condition 2 | Condition 3 | Condition 4 | Condition 5 |
| --- | --- | --- | --- | --- | --- |
| Gold colloid retention amount (A540 max/cm$^2$) | 4.0 | 2.0 | 1.6 | 1.0 | 0.5 |
| Detection limit (cfu/ml) | 400 | 750 | 1000 | 1200 | 7500 |

Example 1: Diagnosis of Diary Cows Suffering from Mastitis Caused by *Escherichia coli*

Evaluation was performed for milk samples collected in a dairy farm by using the immunochromatographic device satisfying the conditions 1 to 5. The bacterial numbers of coliform bacteria contained in the milks as the samples are shown in the following table.

TABLE 2

|  | Individual No. | Detected bacteria | Bacterial number (cfu/ml) |  | Individual No. | Detected bacteria | Bacterial number (cfu/ml) |
| --- | --- | --- | --- | --- | --- | --- | --- |
| Positive cows (developing mastitis) | A | Coliform bacteria | 100000 | Negative cows (not developing mastitis) | F | Coliform bacteria | 600 |
|  | B |  | 4000 |  | G | Coliform bacteria | 400 |
|  | C |  | 3000 |  | H | Coliform bacteria | 350 |
|  | D |  | 2000 |  | I | None | 0 |
|  | E |  | 850 |  | J | Other bacteria | 0 |

As shown in the following table, it was found that, in the case of the conditions 2 to 4, both the sensitivity and specificity exceeded 80%, and mastitis could be appropriately diagnosed. On the other hand, in the case of the condition 1, of which detection limit was low, the result was that *Escherichia coli* bacteria contaminated from the environment were also detected, which provided false positive for non-developing cows, and thus the specificity decreased. Further, when the condition 5 was used, of which detection limit is high, the result was that the specificity was good, but the bacteria could not be detected in the samples from positive cows having *Escherichia coli* bacteria in a small amount, and thus clinical sensitivity was low.

TABLE 3

| | | Condition 1 | Condition 2 | Condition 3 | Condition 4 | Condition 5 |
|---|---|---|---|---|---|---|
| Positive cow | A | + | + | + | + | + |
| | B | + | + | + | + | + |
| | C | + | + | + | + | − |
| | D | + | + | + | + | − |
| | E | + | + | + | − | − |
| Negative cow | F | + | − | − | − | − |
| | G | + | − | − | − | − |
| | H | + | − | − | − | − |
| | I | − | − | − | − | − |
| | J | − | − | − | − | − |
| Diagnostic sensitivity | | 100% | 100% | 80% | 80% | 40% |
| Specificity | | 40% | 100% | 100% | 100% | 100% |

Figure 4:
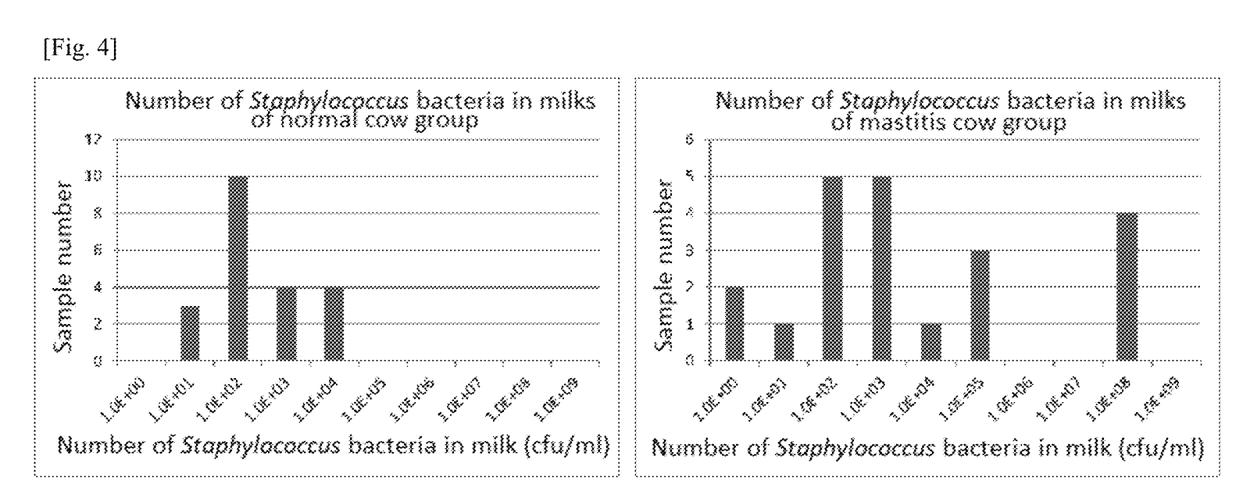
FIG. 4 Numbers of *Staphylococcus* bacteria in milks of normal cow group (left) and mastitis group (right). For example, the column of "1.0E+00" indicates the number of samples in which number of the bacteria was not smaller than $1.0 \times 10^0$ cfu/ml and lower than $1.0 \times 10^1$ cfu/ml. The same shall apply to the other columns.

Example 2: Consideration of Cutoff Value for Cows Suffering from Mastitis Caused by *Staphylococcus* Bacteria, and Diagnosis of them When bacterial numbers of *Staphylococcus* bacteria in milks of individuals that developed clinical mastitis in a dairy firm were evaluated, the results were as shown in FIG. 4.

In the same manner as in the case of *Escherichia coli* mentioned above, ROC analysis was performed, and with changing the bacterial amounts in the milks of the normal group and mastitis group, sensitivity, specificity, positive predictive value, and negative predictive value were calculated by the ROC analysis.

Figure 5:
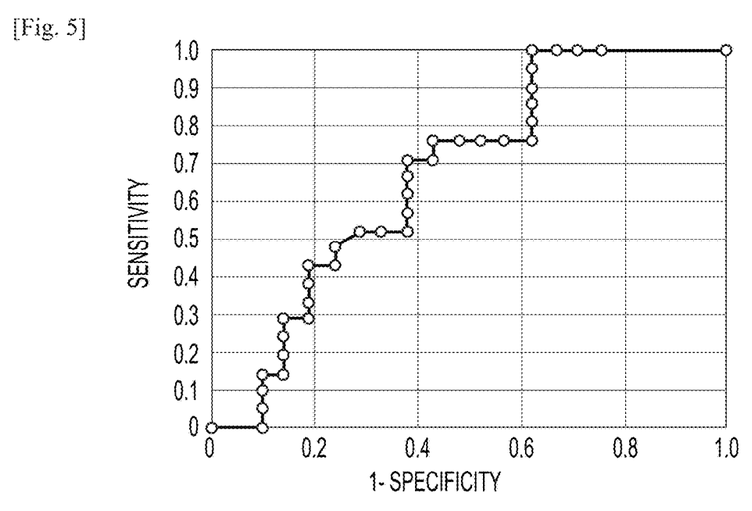
FIG. 5 A mastitis ROC curve (upper part) and a graph showing sensitivity, specificity, positive predictive value, and negative predictive value obtained for mastitis (lower part), for the case where the causative bacterium is a *Staphylococcus* bacterium.

The ROC curve was shown in the upper part of FIG. 5. When bacterial amounts in milks providing a value of 50% or higher for all of sensitivity, specificity, positive predictive value, and negative predictive value were determined as the determination values of the normal group and mastitis group, the range thereof was 375 to 1595 (cfu/ml) (FIG. 5, lower part). When bacterial amounts in milks providing a value of 55% or higher for all of sensitivity, specificity, positive predictive value, and negative predictive value were determined as the determination values of the normal group and mastitis group, the range thereof was 875 to 1145 (cfu/ml).

Reference Example 1: Inspection of Cows Suffering from Mastitis Caused by *Staphylococcus aureus*

Figure 6:
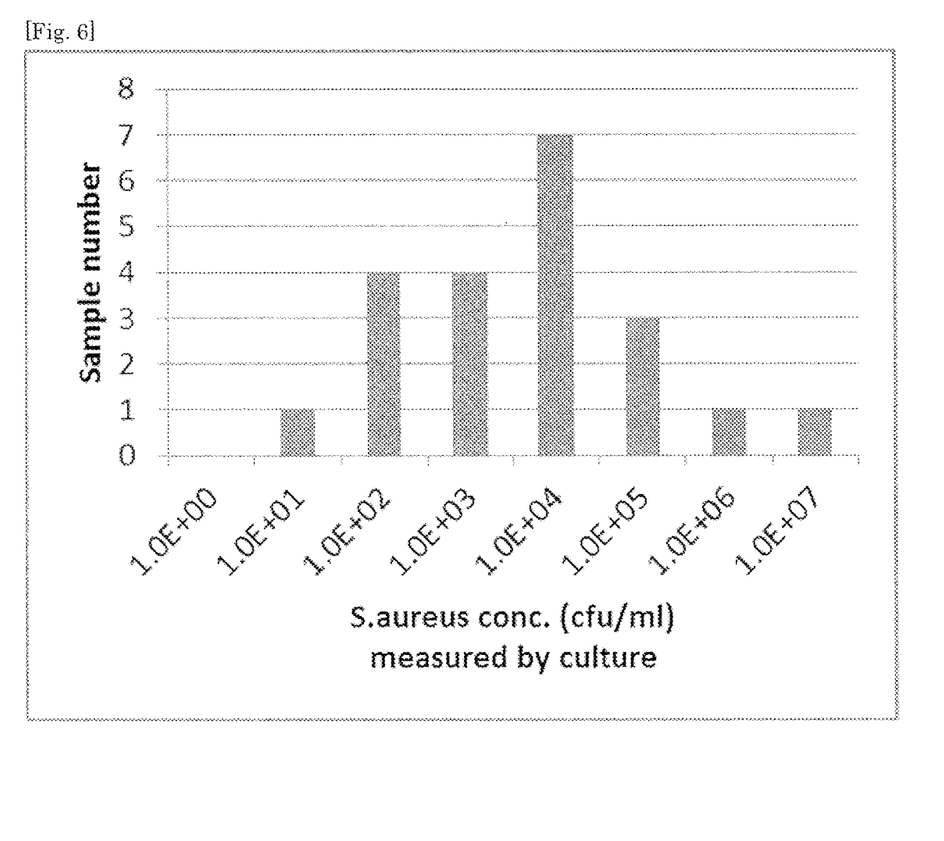
FIG. 6 Numbers of *Staphylococcus aureus* in milks of cow individuals that developed clinical type mastitis.

When the bacterial numbers of *Staphylococcus aureus* in milks of individuals that developed clinical mastitis in a dairy farm were evaluated, the results were as shown in FIG. 6.

In the case of *Staphylococcus aureus* that causes infectious mastitis, if the bacterium is detected, the cow is regarded as infected by the bacterium, unlike the case of the environmental bacterium, *Escherichia coli*. Therefore, a more improved detection limit of the immunochromatographic device (that is, lower bacterial number as the detection limit) should provide higher clinical sensitivity.

INDUSTRIAL APPLICABILITY

The present invention can be used for appropriate diagnosis of mastitis.

DESCRIPTION OF NOTATIONS

1. Labeled antibody-impregnated member
2. Membrane carrier for development
3. Capturing part (test line)
4. Filter member
5. Absorption member
6. Substrate
7. Filter member
8. Capturing part (control line)

The invention claimed is:

1. A method for detecting a causative bacterium of environmental mastitis of a livestock animal, which causative bacterium is any one selected from the group consisting of a coliform bacterium, a *Streptococcus* bacterium a *Klebsiella* bacterium, and a coagulase-negative *Staphylococcus* bacterium, the method comprising:
    determining by an immunological test method whether number of the causative bacterium in a milk of a subject livestock animal is not smaller than a determination value defined beforehand on the basis of distribution of amounts of the causative bacterium in milks derived from a non-disease group and distribution of amounts of the causative bacterium in milks derived from a clinical type mastitis group,
    wherein the immunological test method is an immunochromatographic method using a gold colloid particle-labeled antibody-impregnated member having an antibody labeled with gold colloid particles with a gold colloid retention amount (Amax/cm$^2$) of not less than 0.6/cm$^2$ and not more than 3.5/cm$^2$,
    wherein Amax/cm$^2$ is calculated by dividing maximum absorbance (Amax) of gold colloid eluted from an of area the gold colloid particle-labeled antibody-impregnated member (cm$^2$) with the area the gold colloid particle-labeled antibody-impregnated member (cm$^2$) from which the gold colloid was eluted.

2. The method according to claim 1, wherein the determination value is not smaller than 370 cfu/ml and not larger than 1600 cfu/ml.

3. The method according to claim 1, wherein the causative bacterium is at least one selected from the group consisting of a coliform bacterium, a *Staphylococcus* bacterium, and a *Klebsiella* bacterium.

4. The method according to claim 1, wherein the subject livestock animal is a livestock animal suffering from clinical type mastitis.

5. An immunochromatographic device comprising:
    a first part having a first antibody, which is labeled with gold colloidal particles and is directed to a specific substance derived from an environmental causative bacterium of mastitis of a livestock animal, which causative bacterium is selected from the group consisting of a coliform bacterium, a *Streptococcus* bacterium, and a coagulase-negative *Staphylococcus* bacterium, wherein the gold colloidal particles have a retention amount not less than 0.6/cm$^2$ and not more than 3.5/cm$^2$, wherein Amax/cm$^2$ is calculated by dividing maximum absorbance (Amax) of gold colloid eluted from an of area the gold colloid particle-labeled antibody-impregnated member (cm$^2$) with the area the gold colloid particle-labeled antibody-impregnated member (cm$^2$) from which the gold colloid was eluted, and
    a second part connected downstream from the first part, on which a second antibody directed to the specific substance is immobilized.

6. The immunochromatographic device according to claim 5, wherein a determination value of the causative bacterium is not smaller than 370 cfu/ml and not larger than 1600 cfu/ml.

7. The immunochromatographic device according to claim 5, wherein lower limit of the retention amount of the gold colloid particles corresponds to a determination value not smaller than 370 cfu/ml and not larger than 1600 cfu/ml defined beforehand on the basis of distribution of numbers of the causative bacterium in milks derived from a non-disease group and distribution of numbers of the causative bacterium in milks derived from a disease group.

8. A kit for diagnosing mastitis of a livestock animal caused by an environmental causative bacterium, the kit comprising the immunochromatographic device according to claim 5.

9. The method according to claim 2, wherein the causative bacterium is at least one selected from the group consisting of a coliform bacterium, a *Staphylococcus* bacterium, and a *Klebsiella* bacterium.

10. The method according to claim 2, wherein the subject livestock animal is a livestock animal suffering from clinical type mastitis.

11. The method according to claim 3, wherein the subject livestock animal is a livestock animal suffering from clinical type mastitis.

12. A kit for diagnosing mastitis of a livestock animal caused by an environmental causative bacterium, the kit comprising the immunochromatographic device according to claim 6.

13. A kit for diagnosing mastitis of a livestock animal caused by an environmental causative bacterium, the kit comprising the immunochromatographic device according to claim 7.

* * * * *